US00PP08351P

United States Patent [19]

Marciel et al.

[11] Patent Number: Plant 8,351

[45] Date of Patent: Aug. 17, 1993

[54] HYBRID TEA ROSE PLANT NAMED DEVCARLOS

[75] Inventors: Stanley G. Marciel; Jeanne A. Marciel, both of Aptos, Calif.

[73] Assignee: DeVor Nurseries, Inc., Watsonville, Calif.

[21] Appl. No.: 919,187

[22] Filed: Jul. 23, 1992

[51] Int. Cl.[5] ..... A01H 5/00

[52] U.S. Cl. ..... Plt./15

[58] Field of Search ..... Plt./15, 11

*Primary Examiner*—Howard J. Locker

*Attorney, Agent, or Firm*—Christie, Parker & Hale

[57] ABSTRACT

A new variety of hybrid tea rose plant producing yellow flowers.

1 Drawing Sheet

SUMMARY OF THE INVENTION

The present invention relates to a new and distinct variety of rose plant of the hybrid tea rose class, which was originated by my crossing as seed and pollen parents two unnamed and unpatented seedlings of our creation. The varietal denomination of this new rose is 'Devcarlos'.

Among the novel characteristics possessed by this new variety which distinguishes it from its parents and all other varieties of which I am aware are its attractive yellow flowers produced on long stems and which have long vase life and a pleasing fragrance.

Asexual reproduction by propagation by budding of the new variety as performed in Watsonville, Calif. shows that the foregoing and other distinguishing characteristics come true to form and are established and transmitted through succeeding propagations.

BRIEF DESCRIPTION OF ILLUSTRATION

The accompanying illustration shows typical specimens of the flowers and vegetative growth of the new variety depicted in color as nearly true as it is reasonably possible to make the same in a color illustrations of this character. Phenotypic expression, including colors, may vary depending upon growing conditions, such as climate, soil, and cultivation conditions.

DETAILED DESCRIPTION OF THE NEW VARIETY

The following is a detailed description of my new variety, with color terminology in accordance with The Royal Horticultural Society Colour Chart (R.H.S.C.C.). The terminology used in the color descriptions herein refers to plate numbers in the aforementioned color chart.

Parentage: Seedling.

*Seed parent.*—Unnamed seedling.

*Pollen parent.*—Unnamed seedling.

Class: Hybrid tea.

The following further horticultural observations were made of specimens grown in greenhouses in Watsonville, Calif. in the months of January through April.

FLOWER

Blooming habit: Recurrent.

A. Bud:

(1) *Size.*—Small.

(2) *Form.*—Pointed.

(3) *Color.*—As sepals first divide, near 17A.

(4) *Sepals.*—Longer than bud, becoming horizontal upon opening then reflex. The sepals are about 1 cm above bud when they first divide; near 144A.

(5) *Peduncle.*—Length — about 8 to 9 cm. Aspect — slightly curved. Strength — sturdy and erect. Color — near 144A.

(6) *Bracts.*—Number — about 1 or 2. Color — near 137A. Form — broadly elliptical with acute tip. Location in relation to flower — approximately 5 to 6 cm. below calyx tube.

B. Bloom:

(1) *Size.*—Average size when fully expanded — about 12 to 14 cm.

(2) *Borne.*—Singly.

(3) *Form.*—High centered at first; becoming cupped as flower opens and slightly ruffled.

(4) *Petalage.*—Number of petals under normal conditions — about 30 to 35.

(5) *Color.*—After sepals divide and petals begin to unfurl, near 18B to 18A; at about ⅓-open flower color near 20B with paler shades on outer petals and deeper tonality where petals bunch; outer petals show some veining with darker tones. Point of petal attachment near 14A. General tonality from a distance is yellow and flower coloring lightens upon aging.

C. Petals:

(1) *Texture.*—Medium, leathery.

(2) *Appearance.*—Inside velvety, smooth, flat; leathery outside, smooth, satiny.

(3) *Form.*—Slightly lobed with abrupt point.

(4) *Arrangement.*—Cupped and arranged shingle-like.

(5) *Petaloids in center.*—Few.

(6) *Persistence.*—Persistent.

(7) *Fragrance.*—Moderate, sweet scent.

(8) *Lasting quality.*—Long lasting as a cut flower, about 8 to 10 days.

REPRODUCTIVE ORGANS

A. Stamens, filaments and anthers:

*Arrangement and color.*—Introrse, regularly arranged around styles. Stamens — near 17B.

B. Anthers:

*Color.*—Near 16C.

C. Filaments:
*Color.*—Near 15A.
D. Pollen:
*Color.*—Near 24A.
E. Styles:
*Color.*—Near 2C, medium length, thin.
F. Stigmas: Near 13 C.
G. Hips:
*Shape.*—globular.
*Size.*—About 3 to 3.5 cm. in width and about 3 cm. in length. Seeds protrude on about ½ of the hips.

PLANT

A. Form: Upright, bushy.
B. Growth: Vigorous, uniform branching.
*Height attained.*—About 180 cm.
C. Foliage: Compound 3 , 5 and 7 leaflets.
(1) *Size.*—Medium.
(2) *Quantity.*—Abundant.
(3) *Color.*—New foliage: Upper side — near 147A. Under side — near 191A. Old foliage: Upper side — near 137A. Under side — near 137C.
(4) *Shape.*—Ovate.
(5) *Texture.*—Upper side — semi-glossy; underside — leathery.
(6) *Edge.*—Serrated.
(7) *Serration.*—Serrate.
(8) *Petiole color.*—Upper side — near 200D. Underside — near 147C.
(9) *Stipules.*—Medium, hairy, adnate.

(10) *Auricle description.*—Slender with small hairs.
(11) *Rachis description.*—Prickles.
(12) *Resistance to disease.*—Blackspot — under greenhouse conditions no blackspot. Mildew — good resistance. Rust — under greenhouse conditions no rust.
D. Wood:
(1) *New wood.*—Color — near 146C. Bark — smooth.
(2) *Old wood.*—Color — near 137C. Bark — smooth.
(3) *Flower stem length from last cutting.*—Including peduncle about 66 cm., average leaving 1 to 5 leaves after cutting.
E. Thorns:
*Quantity (main stalk).*—Ordinary.
*On laterals from stalk.*—Ordinary.
*Form.*—Curved, medium width.
*Length.*—Medium.
*Color.*—Near 175A.
*Position.*—Irregular.
*Prickles.*—Few.
F. Winter hardiness: Wintered well in Watsonville, Calif.

I claim:

1. A new and distinct variety of rose plant of the hybrid tea rose class, substantially as shown and described.

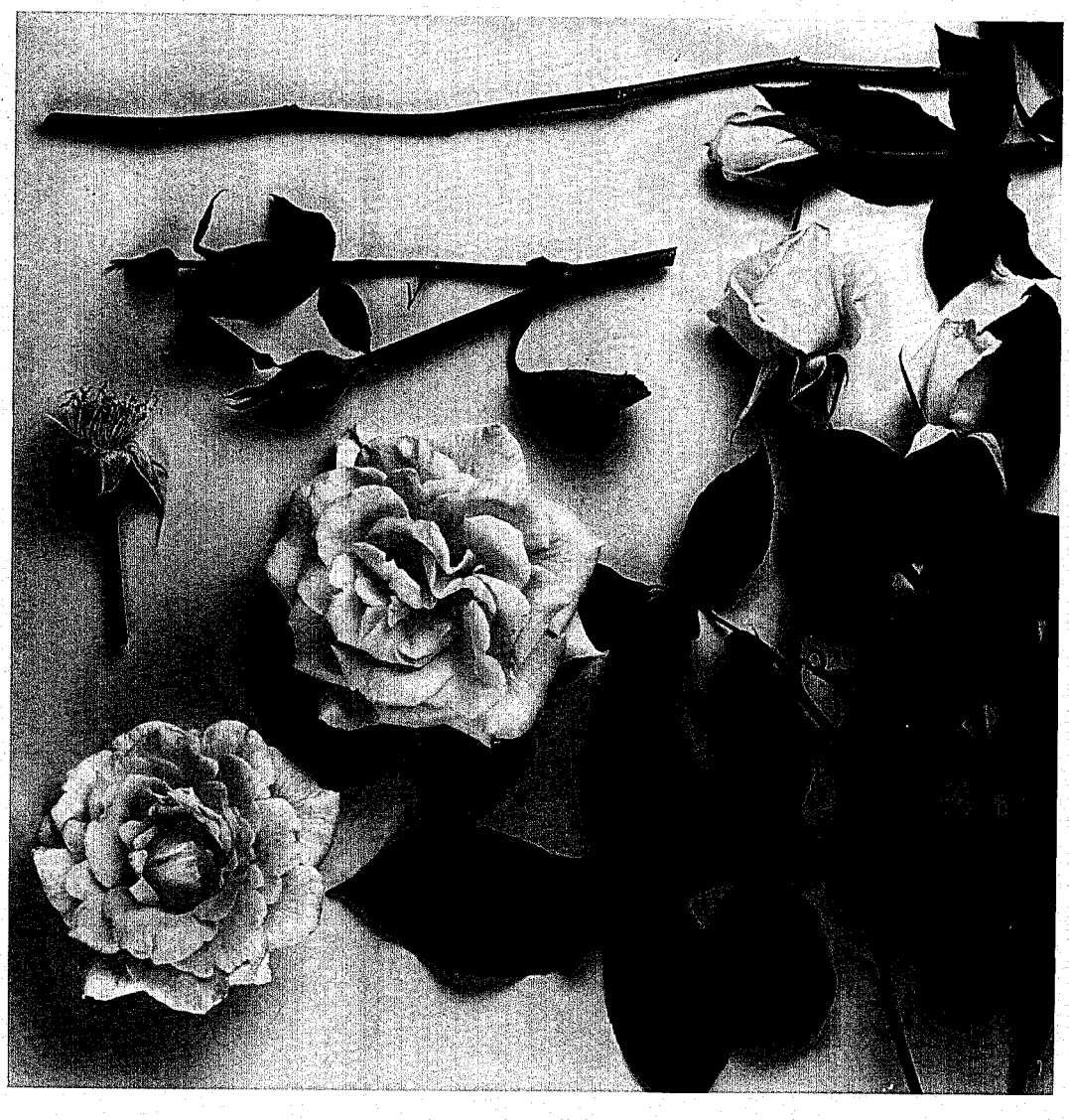

* * * * *